US006666209B2

(12) United States Patent
Bennett et al.

(10) Patent No.: US 6,666,209 B2
(45) Date of Patent: Dec. 23, 2003

(54) METHOD AND SYSTEM OF CALIBRATING AIR FLOW IN A RESPIRATOR SYSTEM

(75) Inventors: Michael R. Bennett, Greenford (GB); David Cook, Bracknell (GB)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/788,786

(22) Filed: Feb. 20, 2001

(65) Prior Publication Data

US 2003/0019494 A1 Jan. 30, 2003

(51) Int. Cl.[7] .............................................. A61M 15/00

(52) U.S. Cl. ............................ 128/200.24; 128/204.21; 128/202.22

(58) Field of Search ....................... 128/200.24, 202.22, 128/204.18, 204.21, 204.23, 204.26

(56) References Cited

U.S. PATENT DOCUMENTS

| | | | | | |
|---|---|---|---|---|---|
| 4,680,956 | A | | 7/1987 | Huszczuk | |
| 4,765,326 | A | * | 8/1988 | Pieper | 128/202.22 |
| 4,899,740 | A | * | 2/1990 | Napolitano | 128/202.22 |
| 5,035,239 | A | * | 7/1991 | Edwards | 128/205.23 |
| 5,199,424 | A | * | 4/1993 | Sullivan et al. | 128/204.18 |
| 5,245,995 | A | * | 9/1993 | Sullivan et al. | 128/204.23 |
| 5,253,640 | A | | 10/1993 | Falb et al. | |
| 5,303,701 | A | | 4/1994 | Heins et al. | 128/206.17 |
| 5,413,097 | A | * | 5/1995 | Birenheide et al. | 128/206.17 |
| 5,522,382 | A | * | 6/1996 | Sullivan et al. | 128/204.23 |
| 5,577,496 | A | * | 11/1996 | Blackwood et al. | 128/201.25 |
| 5,671,730 | A | | 9/1997 | Ollila | 128/204.21 |
| 5,868,133 | A | * | 2/1999 | DeVries et al. | 128/204.21 |
| 5,881,722 | A | * | 3/1999 | DeVries et al. | 128/204.21 |
| 6,135,967 | A | | 10/2000 | Fiorenza et al. | |
| 6,213,119 | B1 | * | 4/2001 | Brydon et al. | 128/204.23 |
| 6,237,592 | B1 | * | 5/2001 | Surjadi et al. | 128/204.23 |
| 6,240,921 | B1 | * | 6/2001 | Brydon et al. | 128/204.18 |
| 6,253,764 | B1 | * | 7/2001 | Calluaud | 128/204.26 |
| 6,332,463 | B1 | * | 12/2001 | Farrugia et al. | 128/204.23 |
| 6,340,025 | B1 | * | 1/2002 | Van Brunt | 128/204.18 |
| 6,398,739 | B1 | * | 6/2002 | Sullivan et al. | 128/204.23 |

FOREIGN PATENT DOCUMENTS

| | | |
|---|---|---|
| GB | 2 008 953 A | 7/1979 |

* cited by examiner

*Primary Examiner*—Aaron J. Lewis
(74) *Attorney, Agent, or Firm*—Kevin W. Raasch; Michaele Hakamaki; Karl G. Hanson

(57) ABSTRACT

A method and apparatus for calibrating the air flow in a respirator system is provided. The method provides for the establishment of control set points in a true calibration protocol through the simple triggering of the microprocessor of a controller. When the trigger is initiated, the microprocessor engages and provides the logic for the calibration cycle. The calibration cycle proceeds until a second trigger terminates the process and establishes the control set points. The calibration sequence of the method relies only on an initiation and termination trigger that is facilitated by components integral to the apparatus.

20 Claims, 4 Drawing Sheets

METHOD AND SYSTEM OF CALIBRATING AIR FLOW IN A RESPIRATOR SYSTEM

TECHNICAL FIELD

The present invention relates to air flow control of blower-based respirators, and more particularly the means by which the set point is established during calibration of the devices.

BACKGROUND OF THE INVENTION

Respiratory breathing systems, particularly blower-based breathing devices, are well known in applications to protect people from respiratory hazards. These respirators typically use a battery powered motor that drives a blower to supply air to the user and are commonly known as Powered Air-Purifying Respirators (PAPRs). PAPR systems are broadly used in industrial environments to protect wearers from various types of hazards, such as particulates, gas, or vapors, which may be encountered in combination.

PAPR systems are often designed to include a number of components. These components are generally able to be exchanged in the field and permit the user to configure the system to meet the needs of a particular application. PAPR components can be divided into two categories; those that are worn by the user and those that deliver air. Components that are worn by the user can include a hood, mask, or shielded helmets, while air delivery components generally include, for example, a filter bank, battery powered blower motor set, air conducting hoses, and hose attachments.

A central element to any PAPR system configuration is the blower motor set. While other components in the system may be changed or varied in some manner, the blower motor set is not generally designed to be reconfigured. The blower motor set must, however, be capable of providing proper air flow through the system regardless of the PAPR configuration. Air flow delivery of the PAPR depends on at least two factors. The first air flow delivery factor arises as a consequence of the system configuration itself. Because each component has an associated pressure drop across it, the cumulative pressure drop across a PAPR system changes as the system components are varied or changed. Changes in pressure drop over the system from one configuration to another will alter the flow delivery capacity of the blower motor set. The second air flow delivery factor involves the operation of the PAPR over time. Time based operational factors that influence air delivery include filter loading and blockage, motor and blower drive component wear and frictional increases, and power loss from the battery. The combination of system and operational flow delivery factors that cause flow variations requires that the air delivery rate of the motor blower set be adjustable to adapt to the variation. To facilitate blower flow delivery adjustment, PAPRs are often equipped with manually operated or automated blower motor control systems. Sophisticated control systems are known that incorporate feedback response to maintain the blower operation in some predetermined condition.

Establishment of a set-point through a calibration protocol is important in any feedback control system. The set point is a synonym for the desired value of a controlled variable such as motor speed or volts supplied to the motor. In a closed-loop system or feedback, the measured value of the controlled variable is returned or "fed back" to a device called a comparator. In the comparator, the controlled variable is compared with the desired value or set point. If there is any difference between the measured variable and the set point, an error is generated. This error enters a controller, which in turn adjusts the final control element in order to return the controlled variable to the set point. The purpose of a calibration protocol is to establish the set point for control.

One way of calibrating a system is through the use of a microprocessor. A general feature of microprocessor-based control systems is that during calibration, the set point is established by logic programmed into the microprocessor at the factory. During field calibration of the units, this generalized logic is called on to establish the set point for control. Calibration of this type could be considered inferential calibration in that the set point is based on inferred logic rather than a true measured flow rate during calibration. The logic is based on generalized performance data established for a particular blower design that has been subjected to known flow restrictions. To field calibrate such a unit, the blower is put into a condition that simulates that employed to establish the calibration logic (e.g., the use of constrictor plates to force a known flow restriction). Under this simulated condition, the control logic can then reestablish the set point for control.

A principal limitation in this type of inferential calibration is that during field calibration, there is no observable measure of true flow performance. Rather, only an inference of the required flow is established. If that inference is inaccurate, an improper calibration could result, which could then lead to potentially undesirable operation of the PAPR unit. In U.S. Pat. No. 5,671,730, for example, a blower's power is regulated on the basis of the current and rotation speed of the blower. A microcontroller is responsive to the blower motor feedback by means of which motor power is regulated. The electronic circuit maintains constant air rate by regulating the pulse-width ratio of the voltage effective across the blower motor. In the described control scheme, calibration and the associated set points are maintained in the control logic of the microcontroller. Once factory established data are incorporated into the nonvolatile read-only memory of the microcontroller, the PAPR is then calibrated by employing specific orifice plates that, with the control device, will bring the blower to the rotation speed which corresponds to the correct flow for a particular blower.

U.S. Pat. No. 5,413,097 describes a fan-supported gas mask and breathing equipment with a microprocessor controlled fan output that uses an inferred calibration protocol. The fan motor is adjusted such that the delivery output of the fan and detection sensor will automatically be adjusted to the necessary filter property, depending on the type of filter employed. In this control scheme, filters are detected by the controller through, for instance, electrical contacts. The blower control then defines set points from pre-established factory supplied data stored in the microprocessor. Co-assigned U.S. Pat. No. 5,303,701 discloses a similar operating scheme but describes an integrated mask, blower, and filter assembly.

A second calibration protocol, which may be referred to as "true calibration", involves the adjustment of the air flow of a PAPR against that of a measured flow rate as indicated by a flow measuring instrument. True calibration protocols are carried out by adjusting the blower motor while the control system is in a calibration mode and the turbo is attached to the flow measuring instrument. Adjustment is carried out by manually varying a potentiometer until the proper air flow is achieved. The logic for adjustment of the potentiometer resides with the technician conducting the calibration. The potentiometer in this case is a "dumb" device that requires knowledge on the part of the technician as to the direction, sensitivity, and degree of adjustment needed. Since no frame of reference for the adjustment is provided, it can be difficult to properly adjust the unit without multiple manipulations of the potentiometer to establish the correct set point. The adjustments often require the use of tools and other components to carry out the calibration, such as specialized keys or screwdrivers. It is not unusual that the PAPR must be at least partially disassembled to permit access to the adjustment element, due to the fragile nature of the potentiometer component. Even without disassembly, the manipulation of small adjustment elements can make the calibration process cumbersome. As may be expected, the industrial environments in which field calibrations are often performed are generally not conducive to fine equipment adjustments. The harsh settings in which PAPRs are typically used (such as many factory or heavily industrial manufacturing settings) can further compound the difficulties of calibration.

A typical calibration procedure might include a technician triggering the control device to set it in calibration mode. The trigger is often done with the aid of an externally applied device such as a magnet held to the blower housing. Once in the calibration mode, the technician manually tunes the potentiometer by rotating a dial or knob. When the proper flow rate is established, the controller is signaled, the set point is established, and the calibration cycle is terminated.

The present invention is directed to the novel integration of a true field calibration procedure and the electronic communication of set point value from that calibration procedure. Communication to the microprocessor, which regulates blower speed during calibration, is facilitated with a simple switching device.

SUMMARY OF THE INVENTION

The present invention relates to a PAPR flow calibration method and apparatus. The method provides for the establishment of control set points in a true calibration protocol through the simple triggering of the microprocessor of a controller. A simple trigger might be a switch that is monitored by the microprocessor. When the trigger is initiated, the microprocessor engages and provides the logic for the calibration cycle. The calibration cycle proceeds until a second trigger terminates the process and establishes the control set points. The calibration sequence of the method relies only on an initiation and termination trigger that is facilitated by components integral to the apparatus. This calibration approach relieves the user of the complexities and knowledge required by prior known potentiometer based calibration systems.

The apparatus of the invention requires no ancillary tools or adjustment elements to carry out a calibration. A simple mechanical switch or electronic gate provides the triggering signal to the microprocessor to start and finish the calibration cycle. The only user provided logic or input is to indicate when to begin and at what point to stop the calibration. In one embodiment, an electronic link might be provided between a flow indicating instrument and the triggering component to terminate the calibration in an automated manner. The simplicity of the calibration procedure combined with the unambiguous nature of a true calibration protocol affords a user the highest level of assurance that proper flow control of the PAPR will be established and maintained.

In one aspect of this invention, a PAPR calibration method is provided, wherein an instrument, independent of the control system, is used to indicate flow rate during the calibration cycle. During calibration, the flow rate of the instrument is monitored, while the blower mower is ramped to a point at which the desired flow rate is reached. Ramping of the motor speed from pre-established speed to the desired rate is accomplished through the microprocessor and is initiated and terminated through a trigger. Once the proper motor speed is attained, the set point is established and the calibration sequence completed. A flow monitoring instrument might be a float-type flow meter that uses a float in a tube. In this case the PAPR, configured for use, would be attached to the flow meter. The individual performing the calibration would then trigger the sequence by, for instance, depressing and holding a switch until the motor speed increases and the desired flow becomes established. Once the proper flow is established, the individual would release the switch, establishing the control set point in the microprocessor and terminating the calibration sequence.

An actuating switch may be manipulated in a number of ways to trigger the microprocessor. For example, the switch might be actuated twice, where the first actuation initiates the calibration cycle and the second actuation triggers the termination of the cycle.

In another embodiment of the invention, an electronic interface between a flow monitoring instrument and the trigger could be used to automate the process. In this case, an individual or a remote signal would trigger the microprocessor to initiate the calibration sequence. A subsequent signal sent from the flow measuring instrument would indicate the termination of the calibration sequence, at which point the microprocessor would determine the control set point and end the calibration cycle. Remote triggering might be facilitated through a radio frequency (RF) type device such as used in RF identification systems. An electronic flow monitoring instrument that might be employed in an automated calibration process would be a flow sensor such as a thermister.

Once a calibration sequence is complete and the proper set point is established, any number of control schemes could be used to maintain proper function of the PAPR during use.

In another aspect of the present invention, a respirator is provided, wherein the respirator comprises a wearer interface element such as a helmet, hood, or face mask that is supplied with air from a delivery system consisting of flow lines, blower unit, baffles and filters. The delivery system employs a microprocessor based blower control means that can be calibrated through a true flow approach with a flow measuring instrument. Calibration set points are established relative to the flow output using the microprocessor with an electronic interface.

BRIEF DESCRIPTION OF THE DRAWINGS

The present invention will be further explained with reference to the appended Figures, wherein like structure is referred to by like numerals throughout the several views, and wherein.

DETAILED DESCRIPTION OF THE PREFERRED EMBODIMENTS

Figure 1:
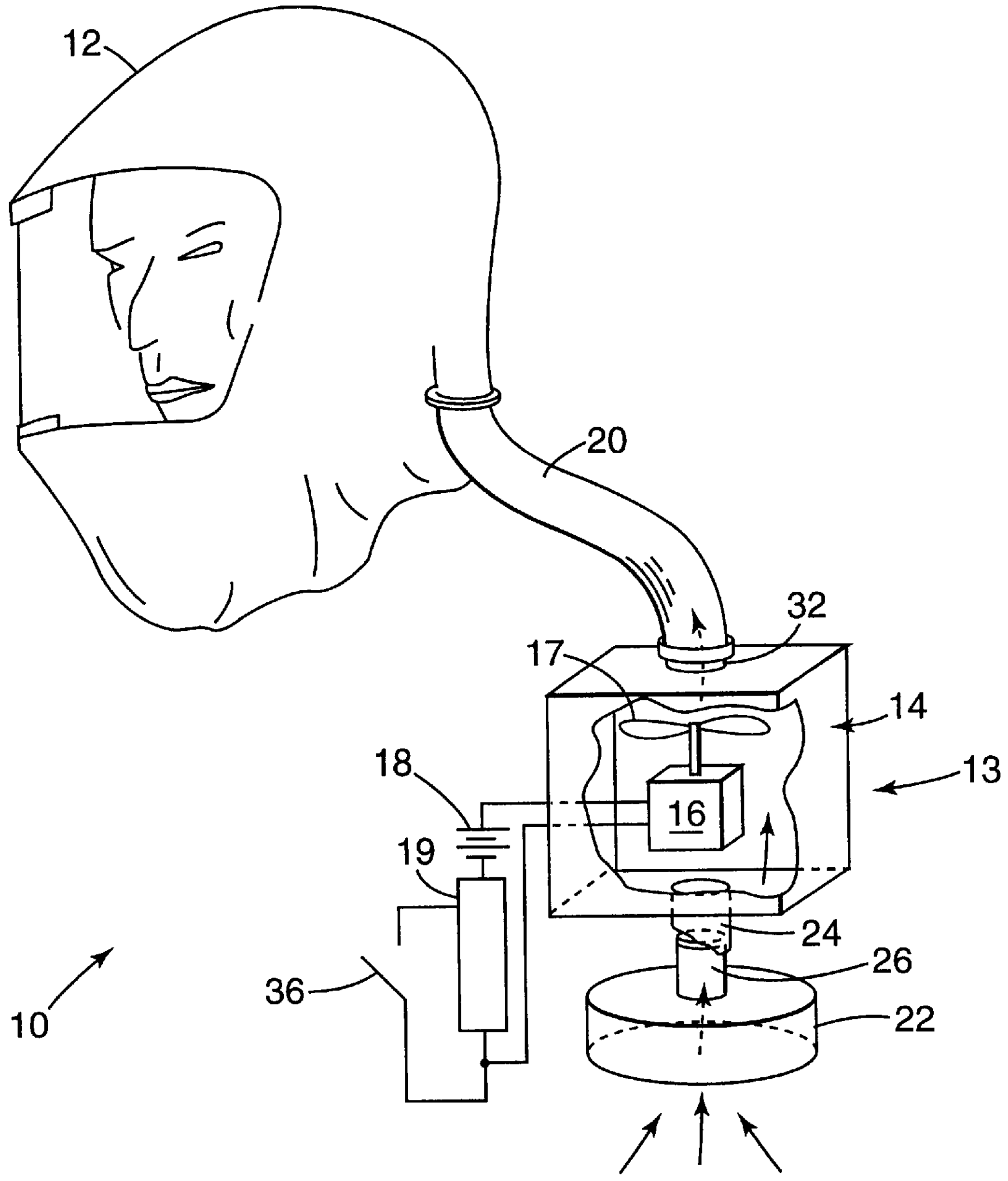
FIG. 1 is a perspective view of a respirator system of the invention.

Referring to the Figures, the powered air-purifying respirator (PAPR) of the present invention is indicated generally as apparatus 10 in FIG. 1. The apparatus 10 may be used for delivering purified air to a user. Apparatus 10 preferably delivers a volume of air at a generally constant flow rate regardless of changes in the configuration of its elements, the operating condition of the system, or the environment in which the apparatus is used. Apparatus 10 includes an air delivery system having a filter bank 22 for removing harmful particulate matter or gas from the air in a particular environment. The filter bank 22 is attached to a blower assembly 13 by way of fittings 24 on a connecting conduit 26 from the filter bank to the blower housing 14. A motor 16 drives a turbine 17 that draws air through the filter bank 22 and delivers it by way of a hose 20 to the component 12 worn by the user. Voltage to the motor is supplied by a battery 18 through a controller 19 that regulates power to the blower motor 16 in response to control signal inputs from a microprocessor integrated into the controller. The microprocessor monitors a switch 36 to determine whether to apply electrical power to the controller and motor.

Figure 2:
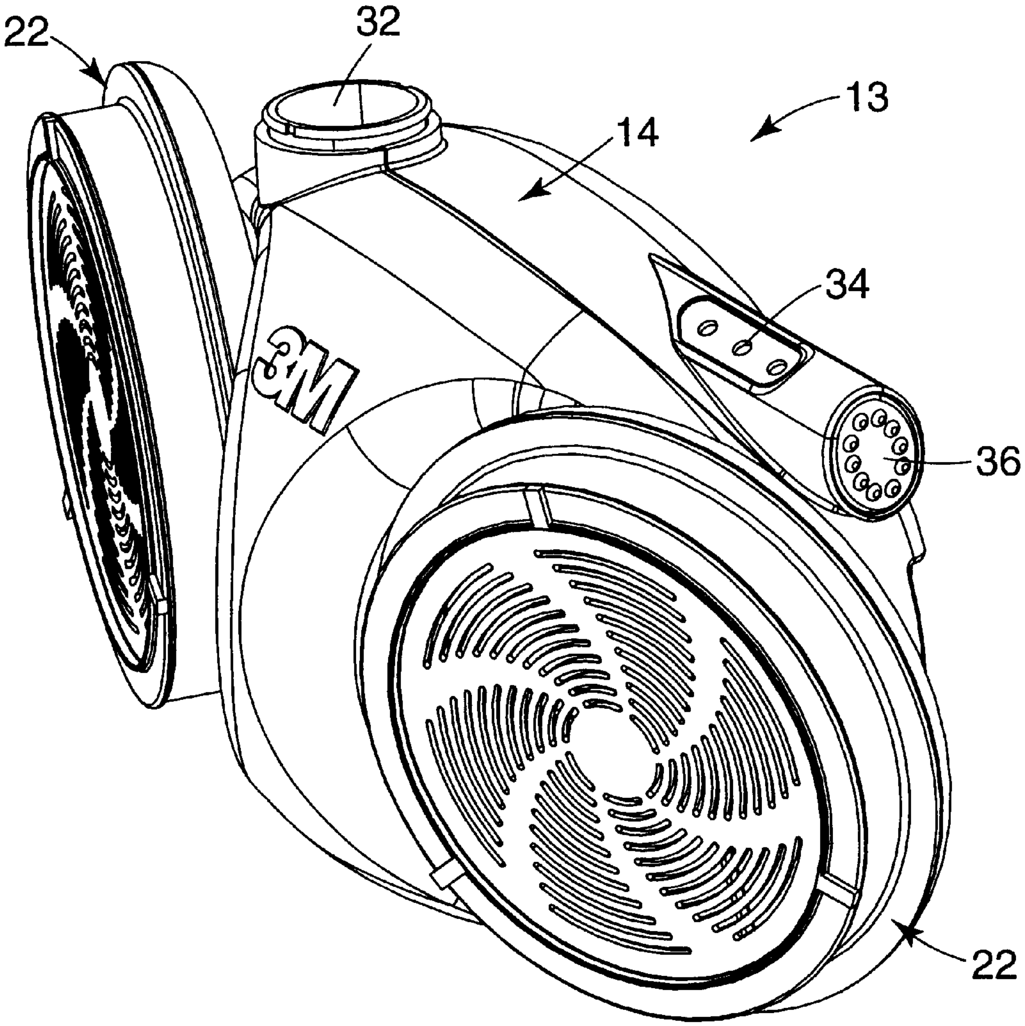
FIG. 2 is a perspective view of a blower housing of the invention.

One configuration of a blower assembly 13 with attached filter banks 22 is shown in FIG. 2. Mounted on top of blower housing 14 is a switch 36 and a group of blower status lights 34. The blower outlet 32 from the blower provides for hose attachment during general use of the respirator or, during calibration, a flow measuring instrument. Operation of the blower unit during both general operation and calibration is facilitated by the switch 36. With general operation, the blower is turned on, for instance, by depressing a button on the switch briefly, after which indicating lights 34 show that the blower is operating within normal limits. To turn the blower off, the switch is actuated again briefly after which the power to the motor is turned off and the indicating lights are no longer activated.

Figure 3:
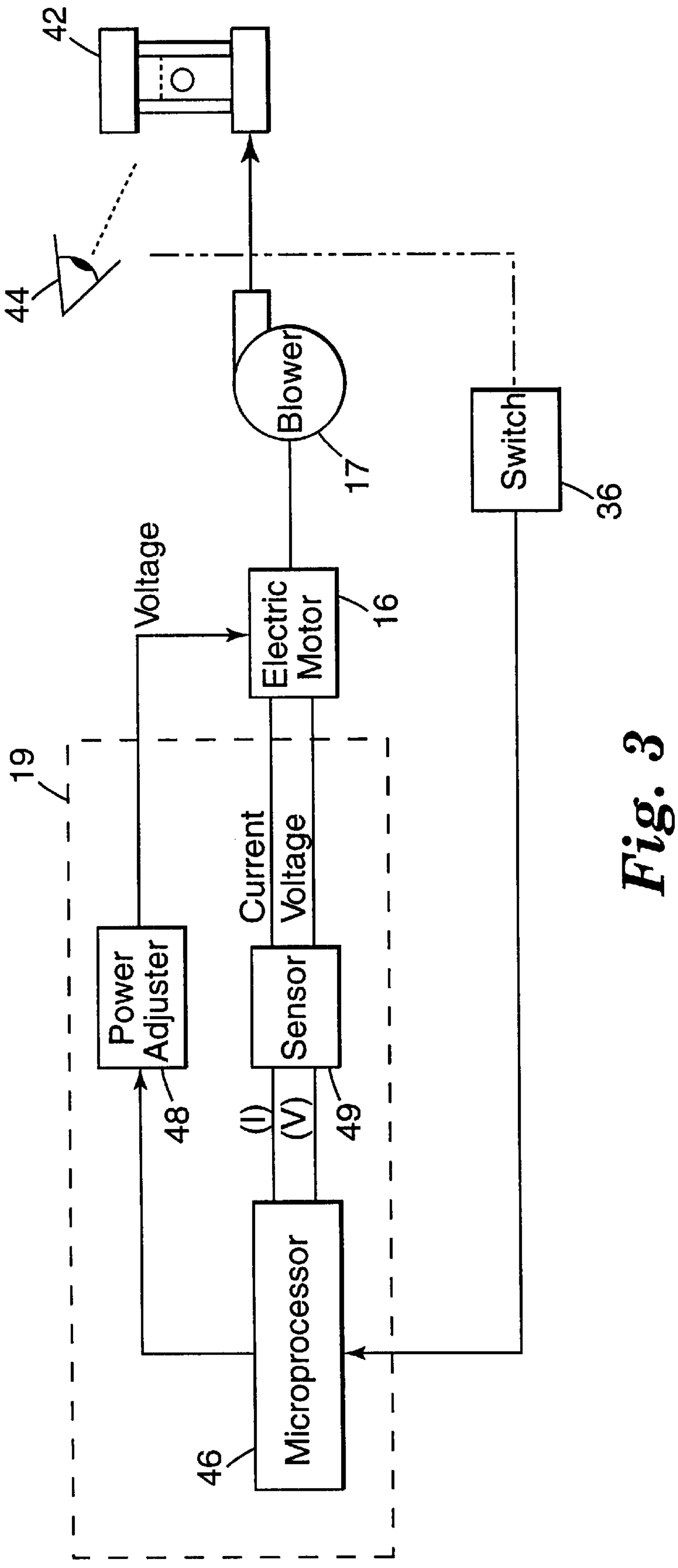
FIG. 3 is a schematic block diagram representative of hardware components constituting an embodiment of the invention.

To calibrate the blower in accordance with one embodiment of the present invention, a flow measuring instrument 42, indicated in FIG. 3, is attached to the blower outlet 32. The measuring instrument 42 is observed by an operator 44 during the calibration process. The measuring instrument 42 may be one of many designs. In the illustrated embodiment, a ball-in-tube type flow measurement instrument is shown. To begin the calibration cycle, the switch 36 is actuated or depressed and held until the signal from the actuated switch is interpreted by the microprocessor 46 as a first trigger, thus initiating the calibration cycle. Immediately after the trigger is sensed, the microprocessor instructs the controller to set the blower motor to a first or base line speed. Calibration may then be indicated by the continual flashing of the indicating lights The base line speed is set below that of what might be encountered during normal operation of the PAPR and results in a blower output of approximately 110 l/min, in one representative example. With continued activation of the switch 36, the blower motor is automatically accelerated by the controller, as specified by the microprocessor. Again, in one example, the motor is accelerated to increase the blower delivery at the rate of 3.2 l/second. Preferably, the acceleration is at a constant rate.

During the calibration cycle the operator keeps the switch 36 actuated while observing the flow indicating instrument 42. The operator releases the switch when a determination has been made that the proper flow rate is reached. This may occur, for example, when the float in the flow instrument reaches a calibration line. The microprocessor interprets the release of the switch as the second trigger in the calibration cycle. When the second trigger is detected the microprocessor captures the control set point. The set point is captured by the microprocessor from inputs for current (I) and voltage (V) as indicated by a sensor 49. The sensor 49 measures the operating conditions of the motor 16 when the second trigger is sensed by the microprocessor 46, which thereby determines the control set point of the system. After the set point is captured by the microprocessor, the microprocessor then completes the calibration cycle and shifts the control of the blower into general operation. Completion of this cycle may be indicated by an audible tone.

While the above description contemplates the base line speed of the motor being a relatively low speed that is subsequently accelerated to achieve a desired result, it is also contemplated that the base line speed of the motor is relatively high and that it is subsequently decelerated to achieve a desired result. In either case, it is preferable that the speed of the motor is varied at a constant rate.

Figure 4:
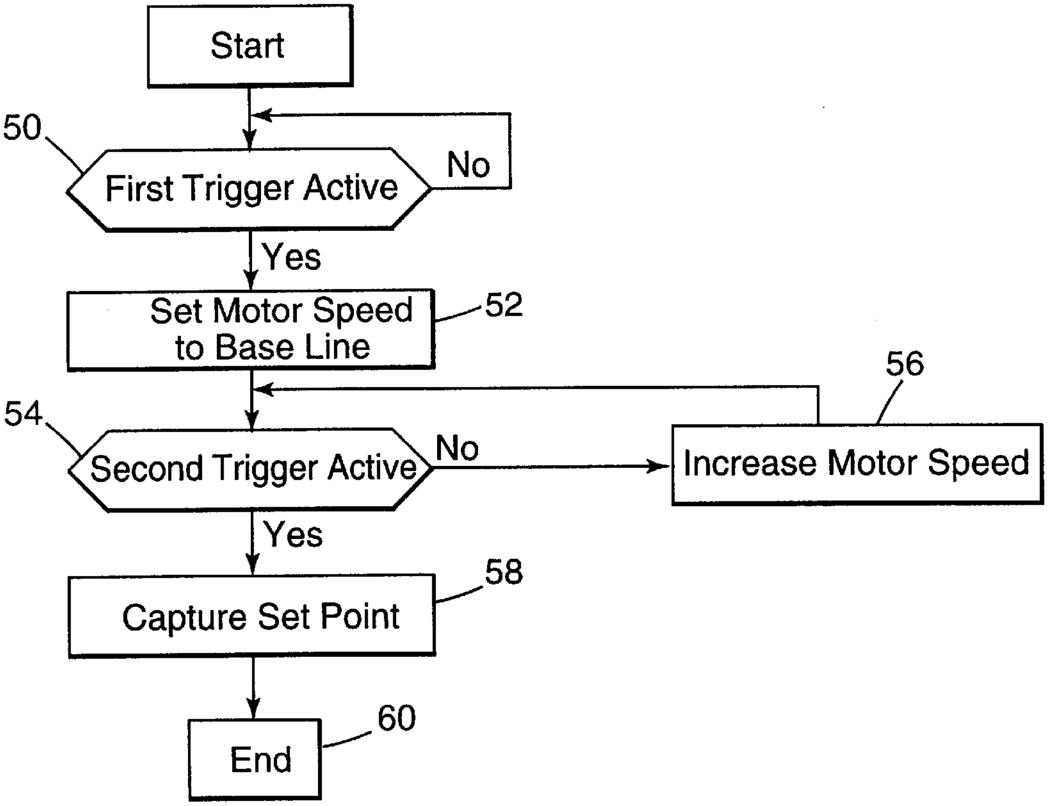
FIG. 4 is a schematic block diagram of representative computational steps in the performance of the embodiment.

Referring again to the flow diagram of FIG. 4, the logic and computational steps therein further describe the inventive calibration method. These steps are performed by the motor controller with the logic for the steps stored in the microprocessor. Step 50 determines whether the first calibration sequence trigger is active. The microprocessor determines activation by sensing the trigger signal and assessing if certain cycle initiating criterion have been met. If the cycle initiating criterion has been met, for instance, by activation of a switch for a specified time period, the calibration will begin. It should be noted that the device used to signal the microprocessor and establish the trigger criterion could take many forms. The trigger signal could be established by various mechanical switching devices such as toggles, rotary switches, touch pads, relays, or the like. It would further be possible to employ a transmitted signal to establish the microprocessor trigger. A receiver for sound waves to actuate voice recognition commands and receivers for radio waves or detectors of magnetic fields could also be used. If the first trigger is active and the condition of step 50 satisfied, the controller in step 52 will set the blower motor to a base line speed which is below that which might be encountered during normal operation. Should the first trigger in step 50 not be active, the microprocessor will continue to monitor the trigger activity.

Subsequent to step 52 and the establishment of a base line speed, the microprocessor determines if a second trigger signal is active in step 54. If no second trigger is sensed by the microprocessor, the controller stepwise accelerates the speed of the motor through a programmed increment in step 56. The loop incorporating steps 54 and 56 are iterated until the microprocessor senses that the second trigger has been activated. When the trigger of step 54 is satisfied, no further acceleration is imparted to the blower motor. With step 54 satisfied the microprocessor retains in its memory the values of operating parameters provided by the controller sensor 49. The values of the operating parameters retained in the memory of the microprocessor when the second trigger is initiated become the control set point for feed-back control. After the set point is captured in this manner the microprocessor signals the end of the calibration cycle and reverts the controller to normal operation. It is important to note that motor parameter values illustrated in the example were voltage and current, but that a number of parameter values could be employed for this purpose. Blower speed, motor torque, or sensor signals from flow sensors, for example, could be used as the basis for a control parameter. It is one of the principal aspects of the present invention that, regardless of the control scheme employed, the method as described remains viable.

The present invention has now been described with reference to several embodiments thereof. The entire disclosure of any patent or patent application identified herein is hereby incorporated by reference. The foregoing detailed description has been given for clarity of understanding only. No unnecessary limitations are to be understood therefrom. It will be apparent to those skilled in the art that many changes can be made in the embodiments described without departing from the scope of the invention. The scope of the present invention should not be limited to the method and apparatus described herein, but only by the method and apparatus described by the language of the claims and the equivalent of the method and apparatus.

What is claimed is:

1. A method of calibrating the air flow in a respirator system having a blower with a motor and a controller having a microprocessor, the method comprising:

providing a first triggering signal to the microprocessor to begin a calibration cycle;

using the first triggering signal to set the motor to a first speed by the controller;

varying the motor speed by the controller;

providing a second triggering signal to the microprocessor to end the calibration cycle and to establish a control set point; and monitoring air flow from the blower while varying the motor speed.

2. The method of claim 1, wherein the respirator system comprises a powered air-purifying respirator.

3. The method of claim 1, wherein establishing a control set point comprises measuring and storing at least one of a set of measured parameters related to control of the motor.

4. The method of claim 3, wherein the measured parameters include at least one of the current through the motor, the voltage across the motor, the speed of the motor, and air flow.

5. The method of claim 1, wherein the first and second triggering signals are provided by a mechanical switch.

6. The method of claim 1, wherein the first and second triggering signals are provided by an electronic gate.

7. The method of claim 1, wherein the flow rate monitoring is performed with a flow meter.

8. The method of claim 1, wherein the step of varying the motor speed includes acceleration of the motor speed.

9. The method of claim 1, wherein the step of varying the motor speed includes decelerating the motor speed.

10. The method of claim 1, wherein the step of varying the motor speed includes varying the motor speed at a constant rate.

11. A method for capturing a control set point in the calibration of a feedback control system of a respiratory system, the method comprising the steps of:

providing a respirator system having a blower with a motor and a controller having a microprocessor;

triggering the microprocessor to begin a calibration cycle;

establishing a first motor speed by the controller;

accelerating the motor speed by the controller;

triggering the microprocessor to capture the control set point and end the calibration cycle; and monitoring air flow from the blower while accelerating the motor speed.

12. A respirator system for supplying air to a user, the respirator system comprising a blower with a motor and a controller having a microprocessor, wherein the flow of air to the user is calibrated by providing a first triggering signal to the microprocessor to begin a calibration cycle, using the first triggering signal to set the motor to a first speed by the controller, varying the motor speed by the controller, providing a second triggering signal to the microprocessor to end the calibration cycle and to establish a control set point, and monitoring air flow from the blower while varying the motor speed.

13. A method of calibrating air flow in a powered air purifying respirator system, the method comprising:

initiating a calibration cycle by providing a first triggering signal to a microprocessor in a controller of a blower motor driving a blower in the powered air purifying respirator system;

changing speed of the blower motor using the controller after initialing the calibration cycle;

monitoring air flow in the powered air purifying system while changing the speed of the blower motor;

terminating the calibration cycle by providing a second triggering signal to the microprocessor; and monitoring and storing at least one motor parameter for the blower motor to establish a control set point.

14. A method according to claim 13, further comprising providing the second triggering signal when the air flow in the powered air purifying system reaches a desired flow rate.

15. A method according to claim 13, wherein monitoring air flow in the powered air purifying system comprises monitoring the air flow using a flow measuring instrument, and further wherein the second triggering signal is provided to the microprocessor by a human operator monitoring the flow measuring instrument.

16. A method according to claim 13, wherein monitoring air flow in the powered air purifying system comprises monitoring the air flow using a flow measuring instrument, and further wherein the second triggering signal is provided to the microprocessor by the flow measuring instrument when the air flow from the blower reaches a desired flow rate.

17. A method according to claim 13, wherein storing at least one motor parameter for the blower motor to establish a control set point occurs alter providing the second triggering signal to the microprocessor.

18. A method according to claim 13, wherein changing speed of the blower motor using the controller comprises increasing the speed of the blower motor from a base line speed.

19. A method according to claim 13, wherein changing speed of the blower motor using the controller comprises decreasing the speed of the blower motor from a base line speed.

20. A powered air purifying respirator system for supplying air to a user, the system comprising a blower, a blower motor driving the blower, and a controller comprising a microprocessor controlling the blower motor, wherein air flow to the user is calibrated by initiating a calibration cycle by providing a first triggering signal to the microprocessor; changing speed of the blower motor using the controller after initiating the calibration cycle; monitoring air flow in the powered air purifying system while changing the speed of the blower motor; terminating the calibration cycle by providing a second triggering signal to the microprocessor; and monitoring and storing at least one motor parameter for the blower motor to establish a control set point.

* * * * *

UNITED STATES PATENT AND TRADEMARK OFFICE

CERTIFICATE OF CORRECTION

PATENT NO. : 6,666,209 B2
DATED : December 23, 2003
INVENTOR(S) : Bennett, Michael R.

It is certified that error appears in the above-identified patent and that said Letters Patent is hereby corrected as shown below:

Column 8,
Line 18, "initialing" should read as -- initiating --.
Line 43, "alter" should read as -- after --.

Signed and Sealed this

Thirteenth Day of April, 2004

JON W. DUDAS
*Acting Director of the United States Patent and Trademark Office*